(12) United States Patent
Martinez et al.

(10) Patent No.: US 6,861,409 B2
(45) Date of Patent: Mar. 1, 2005

(54) GROWTH HORMONE SECRETAGOGUES

(75) Inventors: Jean Martinez, Saussan (FR); Jean-Alain Fehrentz, St. Nazaire de Pezan (FR); Vincent Guerlavais, Montpellier (FR)

(73) Assignee: Zentaris AG, Frankfurt am Main (DE)

( * ) Notice: Subject to any disclaimer, the term of this patent is extended or adjusted under 35 U.S.C. 154(b) by 414 days.

(21) Appl. No.: 09/880,498

(22) Filed: Jun. 13, 2001

(65) Prior Publication Data

US 2002/0165343 A1 Nov. 7, 2002

Related U.S. Application Data

(60) Provisional application No. 60/234,928, filed on Sep. 26, 2000, and provisional application No. 60/211,326, filed on Jun. 13, 2000.

(51) Int. Cl.$^7$ .............................................. A61K 38/00
(52) U.S. Cl. ....................................................... 514/19
(58) Field of Search ........................................... 514/19

(56) References Cited

U.S. PATENT DOCUMENTS 6,025,471 A * 2/2000 Deghenghi et al.

FOREIGN PATENT DOCUMENTS

| WO | WO 95/14666 | 6/1995 |
| WO | WO 96/15148 | 5/1996 |

OTHER PUBLICATIONS

Paris et al., Tetrahedron Letters, 39, 7287–90, 1998.*
McDowell, R.S., et al., "Growth hormone secretagogues: characterization, efficacy, and minimal bioactive conformation," Proc. Nat'l Acad. Sci. USA, 92 (24): 11165–11169 (1995). (Abstract).
Patchett et al., A.A., "Design and biological activities of L–163,191 (MK–0677): A potent, orally active growth hormone secretagogue," Proc. Nat'l. Acad. Sci. USA, 92 (15): 7001–7005, Jul. 1995.
Muccioli, G., et al. "Tissue Distribution of GHRP Receptors in Humans," Abstracts IV European Congress of Endocrinology, Sevilla, Spain, 1998.
Deghenghi R., et al., "Impervious peptides as growth hormone secretagogues," Pept. Sci.: Present, Future, Proc. Int. Pept. Symp., pp. 411–412, 1999. (Abstract).

C. Bowers, "Zenobiotic Growth Hormone Secretagogues: Growth Hormone Releasing Peptides", Eds. B. Bercu and R.F. Walker, Springer–Verlag, pp. 9–28, New York (1996).
R. Deghenghi, "Growth Hormone Releasing Peptides", pp. 85–102 (1996).
R. Deghenghi et al., "Small Peptides as Potent Releasers of Growth Hormone", J. Ped. End. Metab., 8, pp. 311–313 (1996).
R. Deghenghi, "The development of 'impervious peptides' as growth hormone secretagogues", Acta Paediatr Suppl, 423, pp. 85–87 (1997).
E. Ghigo et al., "Growth hormone–releasing peptides", European Journal of Endocrinology, 136, pp. 445–460 (1997).
M. Kojima et al., "Ghrelin is a growth–hormone–releasing acylated peptide from stomach", Nature, 402, pp. 656–660 (1999).
M. Muccioli et al., "Specific receptors for synthetic GH secretagogues in the human brain and pituitary gland", Journal of Endocrinology, 157, pp. 99–106 (1998).
K. Veeraragavan et al., "Growth Hormone–Releasing Peptide (GHRP) Binding to Porcine Anterior Pituitary and Hypothalamic Membranes", Life Sciences, 50, pp. 1149–1155 (1992).

* cited by examiner

Primary Examiner—Michael Meller
(74) Attorney, Agent, or Firm—Winston & Strawn LLP

(57) ABSTRACT

The invention relates to compounds of formula I

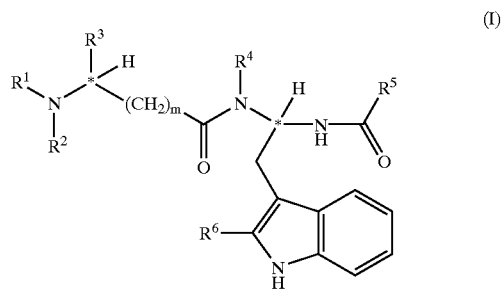

which are useful for elevating the plasma level of growth hormone in a mammal as well for the treatment of growth hormone secretion deficiency, growth retardation in child and metabolic disorders associated with growth hormone secretion deficiency.

9 Claims, No Drawings

SEQUENCE LISTING

```
<160> NUMBER OF SEQ ID NOS: 1

<210> SEQ ID NO 1
<211> LENGTH: 28
<212> TYPE: PRT
<213> ORGANISM: rat
<220> FEATURE:
<221> NAME/KEY: MOD_RES
<222> LOCATION: (3)..(3)
<223> OTHER INFORMATION: o-n-octanoyl

<400> SEQUENCE: 1

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25
```

GROWTH HORMONE SECRETAGOGUES

CROSS-REFERENCE TO RELATED APPLICATIONS

This application claims priority to U.S. provisional application Nos. 60/234,928, filed Sep. 26, 2000, now pending, and 60/211,326, filed Jun. 13, 2000, now pending. The entire disclosure of each prior provisional application is incorporated herein by reference thereto.

FIELD OF THE INVENTION

The invention relates to compounds, which are useful for administration to a mammal thereby elevating the plasma level of growth hormone.

BACKGROUND OF THE INVENTION (a) Description of Prior Art

Growth hormone (GH) or somatotropin, secreted by the pituitary gland constitute a family of hormones which biological activity is fundamental for the linear growth of a young organism but also for the maintenance of the integrity at its adult state. GH acts directly or indirectly on the peripheral organs by stimulating the synthesis of growth factors (insulin-like growth factor-I or IGF-I) or of their receptors (epidermal growth factor or EGF). The direct action of GH is of the type referred to as anti-insulinic, which favors the lipolysis at the level of adipose tissues. Through its action on IGF-I (somatomedin C) synthesis and secretion, GH stimulates the growth of the cartilage and the bones (structural growth), the protein synthesis and the cellular proliferation in multiple peripheral organs, including muscles and the skin. Through its biological activity, GH participates within adults at the maintenance of a protein anabolism state, and plays a primary role in the tissue regeneration phenomenon after a trauma.

The decrease of GH secretion with the age, demonstrated in humans and animals, favors a metabolic shift towards catabolism which initiates or participates to the ageing of an organism. The loss in muscle mass, the accumulation of adipose tissues, the bone demineralization, the loss of tissue regeneration capacity after an injury, which are observed in elderly, correlate with the decrease in the secretion of GH.

GH is thus a physiological anabolic agent absolutely necessary for the linear growth of children and which controls the protein metabolism in adults.

Growth hormone (GH) secretion is regulated by two hypothalamic peptides: GH-releasing hormone (GHRH), which exerts stimulatory effect on GH release and somatostatin which exhibits an inhibitory influence. In the last few years, several investigators have demonstrated that GH secretion can also be stimulated by synthetic oligopeptides termed GH-releasing peptides (GHRP) such as hexarelin and various hexarelin analogs (Ghigo et al., European Journal of Endocrinology, 136, 445–460, 1997). These compounds act through a mechanism which is distinct from that of GHRH (C. Y. Bowers, in "Xenobiotic Growth Hormone Secretagogues", Eds. B. Bercu and R. F. Walker, Pg. 9–28, Springer-Verlag, N.Y. 1996) and by interaction with specific receptors localized in the hypothalamus and pituitary gland ((a) G. Muccioli et al., Journal of Endocrinology, 157, 99–106, 1998; (b) G. Muccioli, "Tissue Distribution of GHRP Receptors in Humans", Abstracts IV European Congress of Endocrinology, Sevilla, Spain, 1998). Recently it was demonstrated that GHRP receptors are present not only in the hypothalamo-pituitary system but even in various human tissues not generally associated with GH release (G. Muccioli et al., see above (a)).

GHRPs and their antagonists are described, for example, in the following publications: C. Y. Bowers, supra, R. Deghenghi, "Growth Hormone Releasing Peptides", ibidem, 1996, pg. 85–102; R. Deghenghi et al., "Small Peptides as Potent Releasers of Growth Hormone", J. Ped. End. Metab., 8, pg. 311–313, 1996; R. Deghenghi, "The Development of Impervious Peptides as Growth Hormone Secretagogues", Acta Paediatr. Suppl., 423, pg. 85–87, 1997; K. Veeraraganavan et al., "Growth Hormone Releasing Peptides (GHRP) Binding to Porcine Anterior Pituitary and Hypothalamic Membranes", Life Sci., 50, Pg. 1149–1155, 1992; and T. C. Somers et al., "Low Molecular Weight Peptidomimetic Growth Hormone Secretagogues, WO 96/15148 (May 23, 1996).

The human GH has been produced by genetic engineering for about ten years. Until recently most of the uses of GH were concerned with growth delay in children and now the uses of GH in adults are studied. The pharmacological uses of GH, GHRPs and growth hormone secretagogues and may be classified in the following three major categories.

(b) Children Growth

Treatments with recombinant human growth hormone have been shown to stimulate growth in children with pituitary dwarfism, renal insufficiencies, Turner's syndrome and short stature. Recombinant human GH is presently commercialized in Europe and in the United States for children's growth retardation caused by a GH deficiency and for children's renal insufficiencies. The other uses are under clinical trial investigation.

(c) Long Term Treatment for Adults and Elderly Patients

A decrease in GH secretion causes changes in body composition during aging. Preliminary studies of one-year treatment with recombinant human GH reported an increase in the muscle mass and in the thickness of skin, a decrease in fat mass with a slight increase in bone density in a population of aged patients. With respect to osteoporosis, recent studies suggest that recombinant human GH does not increase bone mineralization but it is suggested that it may prevent bone demineralization in post-menopausal women. Further studies are currently underway to demonstrate this theory.

(d) Short Term Treatment in Adults and Elderly Patients

In preclinical and clinical studies, growth hormone has been shown to stimulate protein anabolism and healing in cases of bum, AIDS and cancer, in wound and bone healing.

GH, GHRPs and growth hormone secretagogues are also intended for veterinary pharmacological uses. GH, GHRPs and growth hormone secretagogues stimulate growth in pigs during its fattening period by favoring the deposition of muscle tissues instead of adipose tissues and increase milk production in cows, and this without any undesired side effects which would endanger the health of the animals and without any residue in the meat or milk being produced. The bovine somatotropin (BST) is presently commercialized in the United States.

Most of the clinical studies presently undertaken were conducted with recombinant GH. The GHRPs and growth hormone secretagogues are considered as a second generation product destined to replace in the near future the uses of GH in most instances. Accordingly, the use of GHRPs and growth hormone secretagogues present a number of advantages over the use of GH per se.

Therefore, there is a need for compounds which, when administered to a mammal, act as growth hormone secretagogues.

SUMMARY OF THE INVENTION

The present invention relates to new compounds which act as growth hormone secretagogues and, in general, to a method for elevating the plasma level of growth hormone in a mammal by administering thereto one or more of the compounds according to the invention. The invention also relates to methods for the treatment of growth hormone secretion deficiency, for promoting wound healing, recovery from surgery or recovery from debilitating illnesses, by administering to a mammal one of these compounds in a therapeutically effective amount.

DETAILED DESCRIPTION OF THE PREFERRED EMBODIMENTS

In this description, the following abbreviations are used: D is the dextro enantiomer, GH is growth hormone, Boc is tert-butyloxycarbonyl, Z is benzyloxycarbonyl, N-Me is N-methyl, Pip is 4-amino-piperidine-4-carboxylate, Inip is isonipecotyl, i.e. piperidine-4-carboxylate, Aib is α-amino isobutyryl, Nal is β-naphthylalanine, Mrp is 2-Methyl-Trp, and Ala, Lys, Phe, Trp, His, Thr, Cys, Tyr, Leu, Gly, Ser, Pro, Glu, Arg, Val and Gln are the amino acids alanine, lysine, phenylalanine, tryptophan, histidine, threonine, cysteine, tyrosine, leucine, glycine, serine, proline, glutamic acid, arginine, valine and glutamine, respectively. Furthermore gTrp is a group of the formnula

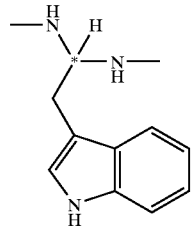

and gMrp a group of the formula

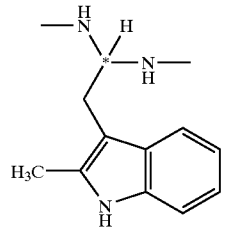

wherein * means a carbon atom which, when a chiral carbon atom, has a R or S configuration. The compounds of the invention are of the general formula I:

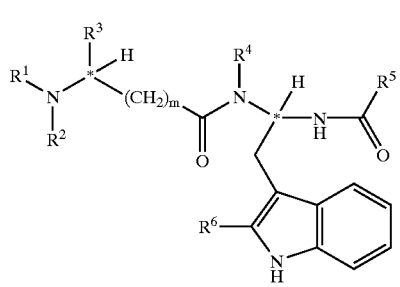

wherein * means a carbon atom which, when a chiral carbon atom, has a R or S configuration, one of $R^1$ and $R^3$ is an hydrogen atom and the other is a group of formula II

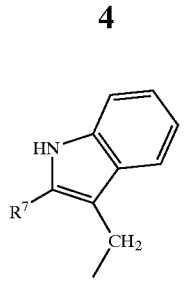

$R^2$ is a hydrogen atom, a linear or branched $C_1$–$C_6$ alkyl group, an aryl group, a heterocyclic group, a cycloalkyl group, a $(CH_2)_n$-aryl group, a $(CH_2)_n$-heterocyclic group, a $(CH_2)_n$-cycloalkyl group, a methylsulfonyl group, a phenylsulfonyl group, a $C(O)R^8$ group or a group according to one or formulas III to VIII below:

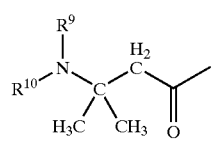

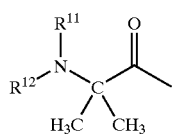

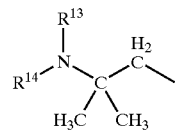

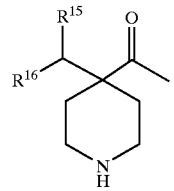

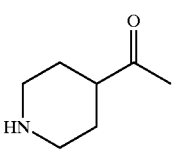

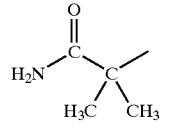

$R^4$ is a hydrogen atom or a linear or branched $C_1$–$C_4$-alkyl group, $R^5$ is a hydrogen atom, a linear or branched $C_1$–$C_4$ alkyl group, a $(CH_2)_n$-aryl group, a $(CH_2)_n$-heterocycle group, a $(CH_2)_n$-cycloalkyl group or an amino group, $R^6$ and $R^7$ are independently from each other a hydrogen atom or a linear or branched $C_1$–$C_4$-alkyl group, $R^8$ is a linear or branched $C_1$–$C_6$-alkyl group, $R^9$, $R^{10}$, $R^{11}$, $R^{12}$, $R^{13}$, $R^{14}$, $R^{15}$, and $R^{16}$ are independ a hydrogen atom or a linear or branched $C_1$–$C_4$-alkyl group, m is 0, 1 or 2 and n is 1 or 2.

A preferred embodiment of the invention are compounds wherein $R^2$ is hydrogen, $R^3$ is a group of formula II and m is 0. Particularly preferred are compounds, wherein linear or branched $C_1$–$C_4$ alkyl is methyl, linear or branched $C_1$–$C_6$ alkyl is methyl, ethyl or i-butyl, aryl is phenyl or naphthyl, cycloalkyl is cyclohexyl and the heterocyclic group is a 4-piperidinyl or 3-pyrrolyl group.

Specifically preferred compounds of the invention include the following:

H-Aib-D-Trp-D-gTrp-CHO:

N-Me-Aib-D-Trp-D-gTrp-C(O)CH$_3$:

N-Me-Aib-D-Trp-N-Me-D-gTrp-C(O)CH$_3$:

In accordance with the present invention, it has been found that the compounds of the invention are useful for elevating the plasma level of growth hormone in a mammal. Furthermore the compounds of the present invention are useful for the treatment of growth hormone secretion deficiency, growth retardation in child and metabolic disorders associated with growth hormone secretion deficiency, in particular in aged subjects.

Pharmaceutically acceptable salts of these compounds can be also used, if desired. Such salts include organic or inorganic addition salts, such as hydrochloride, hydrobromide, phosphate, sulfate, acetate, succinate, ascorbate, tartrate, gluconate, benzoate, malate, fumarate, stearate or pamoate salts.

Pharmaceutical compositions of the invention are useful for elevating the plasma level of growth hormone in a mammal, including a human, as well for the treatment of growth hormone secretion deficiency, growth retardation in child and metabolic disorders associated with growth hormone secretion deficiency, in particular in aged subjects. Such pharmaceutical compositions can comprise a compound according to the present invention or a pharmaceutically acceptable salt thereof, or combinations of compounds according to the present invention or pharmaceutically acceptable salts thereof, optionally in admixture with a carrier, excipient, vehicle, diluent, matrix, or delayed release coating. Examples of such carriers, excipients, vehicles, and diluents, can be found in Remington's Pharmaceutical Sciences, 18th Edition, A. R. Gennaro, Ed., Mack Publishing Company, Easton, Pa., 1990.

The pharmaceutical compositions of the invention can comprise an additional rowth hormone secretagogue. Examples for suitable additional growth hormone ecretagogues are Ghrelin (cf. M. Kojima et al., Nature, 402 (1999), 656–660), GHRP-1, HRP-2 and GHRP-6.

Ghrelin: Gly-Ser-Ser(O-n-octanoyl)-Phe-Leu-Ser-Pro-Glu-His-Gln-Arg-Val-Gln-Gln-Arg-Lys-Glu-Ser-Lys-Lys-Pro-Pro-Ala-Lys-Leu-Gln-Pro-Arg GHRP-1: Ala-His-D-β-Nal-Ala-Trp-D-Phe-Lys-NH$_2$ GHRP-2: D-Ala-D-β-Nal-Ala-Trp-D-Phe-Lys-NH$_2$ GHRP-6: His-D-Trp-Ala-Trp-D-Phe-Lys-NH$_2$ Any of the compounds according to the present invention can be formulated by the skilled in the art to provide medicaments which are suitable for parenteral, buccal, rectal, vaginal, transdermal, pulmonary or oral routes of administration.

The type of formulation of the medicament containing the compound can be selected according to the desired rate of delivery. For example, if the compounds are to be rapidly delivered, the nasal or intravenous route is preferred.

The medicaments can be administered to mammals, including humans, at a therapeutically effective dose which can be easily determined by one of skill in the art and which can vary according to the species, age, sex and weight of the treated patient or subject as well the route of administration. The exact level can be easily determined empirically.

EXAMPLES

The following examples illustrate the efficacy of the most preferred compounds used in the treatment of this invention.

Example 1

H-Aib-D-Trp-D-gTrp-CHO

Total synthesis (percentages represent yields obtained in the synthesis as described below):

Z—D-Trp-OH
98% | 1) IBCF, NMM, DME, 0° C.
     | 2) NH$_4$OH

-continued

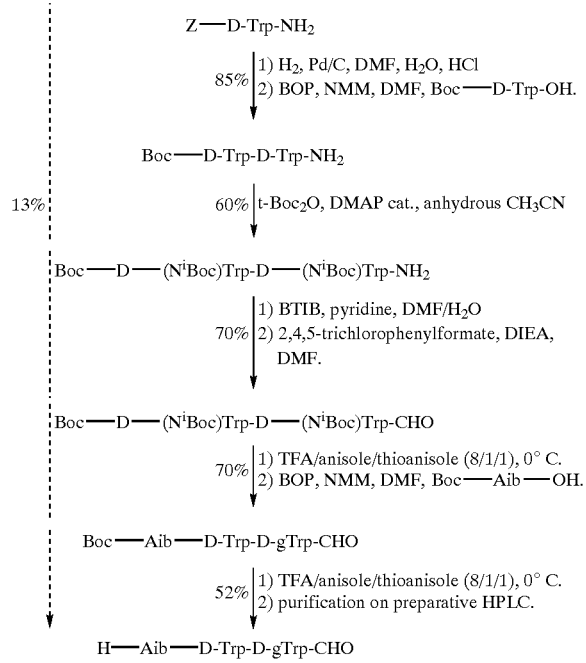

Z-D-Tr-NH$_2$

Z-D-Trp-OH (8.9 g; 26 mmol; 1 eq.) was dissolved in DME (25 ml) and placed in an ice water bath to 0° C. NMM (3.5 ml; 1.2 eq.), IBCF (4.1 ml; 1.2 eq.) and ammonia solution 28% (8.9 ml; 5 eq.) were added successively. The mixture was diluted with water (100 ml), and the product Z-D-Trp-NH$_2$ precipitated. It was filtered and dried in vacuo to afford 8.58 g of a white solid.

Yield=98%.

$C_{19}H_{19}N_3O_3$, 337 g.mol$^{-1}$.

Rf=0.46 {Chloroform/Methanol/Acetic Acid (180/10/5)}.

$^1$H NMR (250 MHZ, DMSO-d$^6$): δ 2.9 (dd, 1H, H$_\beta$, J$_{\beta\beta'}$=14.5 Hz; J$_{\beta\alpha}$=9.8 Hz); 3.1 (dd, 1H, H$_{\beta'}$, J$_{\beta'\beta}$=14.5 Hz; J$_{\beta'\alpha}$=4.3 Hz); 4.2 (sextuplet, 1H, H$_\alpha$); 4.95 (s, 2H, CH$_2$ (Z)); 6.9–7.4 (m, 11H); 7.5 (s, 1H, H$^2$); 7.65 (d, 1H, J=7.7 Hz); 10.8 (s, 1H, N$^1$H).

Mass Spectrometry (Electrospray), m/z 338 [M+H]$^+$, 360 [M+Na]$^+$, 675 [2M+H]$^+$, 697 [2M+Na]$^+$.

Boc-D-Trp-D-Trp-NH$_2$

Z-D-Trp-NH$_2$ (3 g; 8.9 mmol; 1 eq.) was dissolved in DMF (100 ml). HCl 36% (845 μl; 1.1 eq.), water (2 ml) and palladium on activated charcoal (95 mg, 0.1 eq.) were added to the stirred mixture. The solution was bubbled under hydrogen for 24 hr. When the reaction went to completion, the palladium was filtered on celite. The solvent was removed in vacuo to afford HCl, H-D-Trp-NH$_2$ as a colorless oil.

In 10 ml of DMF, HCl, H-D-Trp-NH$_2$ (8.9 mmol; 1 eq.), Boc-D-Trp-OH (2.98 g; 9.8 mmol; 1.1 eq.), NMM (2.26 ml; 2.1 eq.) and BOP (4.33 g; 1.1 eq.) were added successively. After 1 hr, the mixture was diluted with ethyl acetate (100 ml) and washed with saturated aqueous sodium hydrogen carbonate (200 ml), aqueous potassium hydrogen sulfate (200 ml, 1M), and saturated aqueous sodium chloride (100 ml). The organic layer was dried over sodium sulfate, filtered and the solvent removed in vacuo to afford 4.35 g of Boc-D-Trp-D-Trp-NH$_2$ as a white solid.

Yield=85%.

$C_{27}H_{31}N_5O_4$, 489 g.mol$^{-1}$.

Rf=0.48 {Chloroform/Methanol/Acetic Acid (85/10/5)}.

$^1$H NMR (200 MHZ, DMSO-d$^6$): δ 1.28 (s, 9H, Boc); 2.75–3.36 (m, 4H, 2 (CH$_2$)$_\beta$; 4.14 (m, 1H, CH$_\alpha$); 4.52 (m, 1H, CH$_{\alpha'}$); 6.83–7.84 (m, 14H, 2 indoles (10H), NH$_2$, NH (urethane) and NH (amide)); 10.82 (d, 1H, J=2 Hz, N$^1$H); 10.85 (d, 1H, J=2 Hz, N$^1$H).

Mass Spectrometry (Electrospray), m/z 490 [M+H]$^+$, 512 [M+Na]$^+$, 979 [2M+H]$^+$.

Boc-D-(NiBoc)Trp-D-(NiBoc)Trp-NH$_2$

Boc-D-Trp-D-Trp-NH$_2$ (3 g; 6.13 mmol; 1 eq.) was dissolved in acetonitrile (25 ml).

To this solution, di-tert-butyl-dicarbonate (3.4 g; 2.5 eq.) and 4-dimethylaminopyridine (150 mg; 0.2 eq.) were successively added. After 1 hr, the mixture was diluted with ethyl acetate (100 ml) and washed with saturated aqueous sodium hydrogen carbonate (200 ml), aqueous potassium hydrogen sulfate (200 ml, 1M), and saturated aqueous sodium chloride (200 ml). The organic layer was dried over sodium sulfate, filtered and the solvent removed in vacuo. The residue was purified by flash chromatography on silica gel eluting with ethyl acetate/hexane {5/5} to afford 2.53 g of Boc-D-(N$^i$Boc)Trp-D-(N$^i$Boc)Trp-NH$_2$ as a white solid.

Yield=60%.

$C_{37}H_{47}N_5O_8$, 689 g.mol$^{-1}$.

Rf=0.23 {ethyl acetate/hexane (5/5)}.

$^1$H NMR (200 MHZ, DMSO-d$^6$): δ 1.25 (s, 9H, Boc); 1.58 (s, 9H, Boc); 1.61 (s, 9H, Boc); 2.75–3.4 (m, 4H, 2 (CH$_2$)$_\beta$); 4.2 (m, 1H, CH$_\alpha$); 4.6 (m, 1H, CH$_\alpha$); 7.06–8 (m, 14H, 2 indoles (10H), NH (urethane), NH and NH$_2$ (amides)).

Mass Spectrometry (Electrospray), m/z 690 [M+H]$^+$, 712 [M+Na]$^+$, 1379 [2M+H]$^+$, 1401 [2M+Na]$^+$.

Boc-D-(N$^i$Boc)Trp-D-g(N$^i$Boc)Trp-H

Boc-D-(N$^i$Boc)Trp-D-(N$^i$Boc)Trp-NH2 (3 g; 4.3 mmol; 1 eq.) was dissolved in the mixture DMF/water (18 ml/7 ml). Then, pyridine (772 μl; 2.2 eq.) and Bis(Trifluoroacetoxy)IodoBenzene (2.1 g; 1.1 eq.) were added. After 1 hr, the mixture was diluted with ethyl acetate (100 ml) and washed with saturated aqueous sodium hydrogen carbonate (200 ml), aqueous potassium hydrogen sulfate (200 ml, 1M), and aqueous saturated sodium chloride (200 ml). The organic layer was dried over sodium sulfate, filtered and the solvent removed in vacuo. Boc-D-N$^i$Boc)Trp-D-g(N$^i$Boc)Trp-H was used immediately for the next reaction of formylation.

Rf=0.14 {ethyl acetate/hexane (7/3)}.

$C_{36}H_{47}N_5O_7$, 661 g.mol$^{-1}$.

$^1$H NMR (200 MHZ, DMSO-d$^6$): δ 1.29 (s, 9H, Boc); 1.61 (s, 18H, 2 Boc); 2.13 (s, 2H, NH$_2$ (amine)); 3.1–2.8 (m, 4H, 2 (CH$_2$)$_\beta$); 4.2 (m, 1H, CH$_\alpha$); 4.85 (m, 1H, CH$_\alpha$); 6.9–8 (m, 12H, 2 indoles (10H), NH (urethane), NH (amide)).

Mass Spectrometry (Electrospray), m/z 662 [M+H]$^+$, 684 [M+Na]$^+$.

Boc-D-(N$^i$Boc)Trp-D-g(N$^i$Boc)Trp-CHO

Boc-D-(N$^i$Boc)Trp-D-g(N$^i$Boc)Trp-H (4.3 mmol; 1 eq.) was dissolved in DMF (20 ml). Then, N,N-diisopropylethylamine (815 μl; 1.1 eq.) and 2,4,5-trichlorophenylformate (1.08 g; 1.1 eq.) were added. After 30 minutes, the mixture was diluted with ethyl acetate (100 ml) and washed with saturated aqueous sodium hydrogen carbonate (200 ml), aqueous potassium hydrogen sulfate (200 ml, 1M), and saturated aqueous sodium chloride (200 ml). The organic layer was dried over sodium sulfate, filtered and the solvent removed in vacuo. The residue was purified by flash chromatography on silica gel eluting with ethyl acetate/hexane {5/5} to afford 2.07 g of Boc-D-(N$^i$Boc)Trp-D-g(N$^i$Boc)Trp-CHO as a white solid.

Yield=70%.

$C_{37}H_{47}N_5O_8$, 689 g.mol$^{-1}$.

Rf=0.27 {ethyl acetate/hexane (5/5)}.

$^1$H NMR (200 MHZ, DMSO-d$^6$): δ 1.28 (s, 9H, Boc); 1.6 (s, 9H, Boc); 1.61 (s, 9H, Boc); 2.75–3.1 (m, 4H, 2 (CH$_2$)$_\beta$); 4.25 (m, 1H, (CH)α$_{A\&B}$); 5.39 (m, 0.4H, (CH)α'$_B$); 5.72 (m, 0.6H, (CH)α'$_A$); 6.95–8.55 (m, 14H, 2 indoles (10H), NH (urethane), 2 NH (amides), CHO (formyl)).

Mass Spectrometry (Electrospray), m/z 690 [M+H]$^+$, 712 [M+Na]$^+$, 1379 [2M+H]$^+$.

Boc-Aib-D-Trp-D-gTrp-CHO

Boc-D-(N$^i$Boc)Trp-D-g(N$^i$Boc)Trp-CHO (1.98 g; 2.9 mmol; 1 eq.) was dissolved in a -mixture of trifluoroacetic acid (16 ml), anisole (2 ml) and thioanisole (2 ml) for 30 minutes at 0° C. The solvents were removed in vacuo, the residue was stirred with ether and the precipitated TFA, H-D-Trp-D-gTrp-CHO was filtered.

TFA, H-D-Trp-D-gTrp-CHO (2.9 mmol; 1 eq.), Boc-Aib-OH (700 mg; 1 eq.), NMM (2.4 ml; 4.2 eq.) and BOP (1.53 g; 1.2 eq.) were successively added in 10 ml of DMF. After 1 hr, the mixture was diluted with ethyl acetate (100 ml) and washed with saturated aqueous sodium hydrogen carbonate (200 ml), aqueous potassium hydrogen sulfate (200 ml, 1M), and saturated aqueous sodium chloride (200 ml). The organic layer was dried over sodium sulfate, filtered and the solvent removed in vacuo. The residue was purified by flash chromatography on silica gel eluting with ethyl acetate to afford 1.16 g of Boc-Aib-D-Trp-D-gTrp-CHO as a white solid.

Yield=70%.

$C_{31}H_{38}N_6O_5$, 574 g.mol$^{-1}$.

Rf=0.26 {Chloroform/Methanol/Acetic Acid (180/10/5)}.

$^1$H NMR (200 MHZ, DMSO-d$^6$): δ 1.21 (s, 6H, 2 CH$_3$ (Aib)); 1.31 (s, 9H, Boc); 2.98–3.12 (m, 4H, 2 (CH$_2$)$_\beta$); 4.47 (m, 1H, (CH)α$_{A\&B}$); 5.2 (m, 0.4H, (CH)α'$_B$); 5.7 (m, 0.6H, (CH)α'$_A$); 6.95–8.37 (m, 15H, 2 indoles (10H), 3 NH (amides), 1 NH (urethane) CHO (formyl)); 10.89 (m, 2H, 2 N$^1$H (indoles)).

Mass Spectrometry (Electrospray), m/z 575 [M+H]$^+$, 597 [M+Na]$^+$, 1149 [2M+H]$^+$, 1171 [2M+Na]$^+$.

H-Aib-D-Trp-D-gTrT-CHO

Boc-Aib-D-Trp-D-gTrp-CHO (1 g; 1.7 nmmol) was dissolved in a mixture of trifluoroacetic acid (8 ml), anisole (1 ml) and thioanisole (1 ml) for 30 minutes at 0° C. The solvents were removed in vacuo, the residue was stirred with ether and the precipitated TFA, H-Aib-D-Trp-D-gTrp-CHO was filtered.

The product TFA, H-Aib-D-Trp-D-gTrp-CHO was purified by preparative HPLC (Waters, delta pak, C18, 40×100 mm, 5 μm, 100 A).

Yield=52%.

$C_{26}H_{30}N_6O_3$, 474 g.mol$^{-1}$.

$^1$H NMR (400 MHZ, DMSO-d$^6$)+$^1$H/$^1$H correlation: δ 1.21 (s, 3H, CH$_3$ (Aib)); 1.43 (s, 3H, CH$_3$ (Aib)); 2.97 (m, 2H, (CH$_2$)$_\beta$); 3.1 (m, 2H, (CH$_2$)$_{\beta'}$); 4.62 (m, 1H, (CH)α$_{A\&B}$); 5.32 (q, 0.4H, (CH)α'$_B$); 5.71 (q, 0.6H, (CH)α'$_A$); 7.3 (m, 4H$_5$ and H$_6$ (2 indoles)); 7.06–7.2 (4d, 2H, H$_{2A}$ et H$_{2B}$ (2 indoles)); 7.3 (m, 2H, H$_4$ or H$_7$ (2 indoles)); 7.6–7.8 (4d, 2H, H$_{4A}$ and H$_{4B}$ or H$_{7A}$ et H$_{7B}$); 7.97 (s, 3H, NH$_2$ (Aib) and CHO (Formyl));8.2 (d, 0.4H, NH$_{1B}$ (diamino)); 8.3 (m,1H, NH$_{A\&B}$); 8.5 (d, 0.6H, NH$_{1A}$ (diamino)); 8.69 (d, 0.6H, NH$_2$A (diamino)); 8.96 (d, 0.4H, NH$_{2B}$ (diamino)); 10.8 (s, 0.6H, N$^1$H$_{1A}$ (indole)); 10.82 (s, 0.4H, N$^1$H$_{1B}$ (indole)); 10.86 (s, 0.6H, N$^1$H$_2$A (indole)); 10.91 (s, 0.4, N$^1$H$_{2B}$ (indole)).

Mass Spectrometry (Electrospray), m/z 475 [M+H]$^+$, 949 [2M+H]$^+$.

Analogous synthesis were performed for the following compounds:

Example 2

H-Aib-D-Mrp-D-gMrp-CHO $C_{28}H_{34}N_6O_3$, 502 g.mol$^{-1}$.

$^1$H NMR (400 MHZ, DMSO-d$^6$)+$^1$H/$^1$H correlation: δ 1.19 (s, 2H, (CH$_3$)$_{1A}$ (Aib)); 1.23 (s, 1H, (CH$_3$)$_{1B}$ (Aib)); 1.41 (s, 2H, (CH$_3$)$_{2A}$ (Aib)); 1.44 (s, 2H, (CH$_3$)$_{2B}$ (Aib)); 2.33–2.35 (4s, 6H, 2 CH$_3$ (indoles)); 2.93 (m, 2H, (CH$_2$)$_\beta$); 3.02 (m, 2H, (CH$_2$)$_{\beta'}$); 4.65 (m, 0.6H, (CH)α$_A$); 4.71 (m, 0.4H, (CH)α$_B$); 5.2 (m, 0.4H, (CH)α'$_B$); 5.6 (m, 0.6H, (CH)α'$_A$); 6.95 (m, 4H, H$_5$ and H$_6$ (2 indoles)); 7.19 (m, 2H, H$_4$ or H$_7$ (2 indoles)); 7.6 (m, 2H, H$_4$ or H$_7$ (2 indoles)); 7.9 (s, 1H, CHO (Formyl)); 7.95 (s, 2H, NH$_2$ (Aib)); 8.05 (d, 0.4H, NH$_{1B}$ (diamino)); 8.3 (m,1H, NH$_{A\&B}$); 8.35 (m, 0.6H, NH$_{1A}$ (diamino)); 8.4 (d, 0.6H, NH$_{2A}$ (diamino)); 8.75 (d, 0.4H, NH$_{2B}$ (diamino)); 10.69 (s, 0.6H, N$^1$H$_{1A}$ (indole)); 10.71 (s, 0.4H, N$^1$H$_{1B}$ (indole)); 10.80 (s, 0.6H, N$^1$H$_{2A}$ (indole)); 10.92 (s, 0.4H, N$^1$H$_{2B}$ (indole)).

Mass Spectrometry (Electrospray), m/z 503.1 [M+H]$^+$.

Example 3

N-Me-Aib-D-Trp-D-gTrp-CHO

Boc-N-Me-Aib-OH (327 mg; 1.5 mmol; 2.6 eq.) was dissolved in methylene chloride (10 ml) and cooled to 0° C. Then, dicyclohexylcarbodiimide (156 mg; 0.75 mmol; 1.3 eq.) was added. The mixture, after filtration of DCU, was added to a solution containing TFA, H-D-Trp-D-gTrp-CHO (0.58 mmol; 1 eq.) and triethylamine (267 μl; 3.3 eq.) in methylene chloride (5 ml). The reaction mixture was slowly warmed to room temperature and stopped after 24 hr. The mixture was diluted with ethyl acetate (25 ml) and washed with saturated aqueous sodium hydrogen carbonate (50 ml), aqueous potassium hydrogen sulfate (50 ml, 1M), and saturated aqueous sodium chloride (50 ml). The organic layer was dried over sodium sulfate, filtered and the solvent removed in vacuo. The residue was purified by flash chromatography on silica gel eluting with ethyl acetate/methanol {9/1 } to afford 180 mg (53%) of Boc-N-Me-Aib-D-gTrp-CHO as a white foam.

Boc-N-Me-Aib-D-Trp-D-gTrp-CHO (180 mg; 0.3 mmol) was dissolved in a mixture of trifluoroacetic acid (8 ml), anisole (1 ml) and thioanisole (1 ml) for 30 minutes at 0° C. The solvents were removed in vacuo, the residue was stirred with ether and the precipitated TFA, N-Me-Aib-D-Trp-D-gTrp-CHO was filtered.

The product TFA, N-Me-Aib-D-Trp-D-gTrp-CHO (39 mg; 15%) was purified by preparative HPLC (Waters, delta pak, C18, 40×100 nmm, 5 μm, 100 A).

$C_{27}H_{32}N_6O_3$, 488 g.mol$^{-1}$.

$^1$H RMN (200 MHZ, DMSO-d$^6$): δ 1.19 (s, 3H, CH$_3$ (Aib)); 1.42 (s, 3H, CH$_3$ (Aib)); 2.26 (s, 3H, NCH$_3$); 3.12 (m, 4H, 2 (CH$_2$)$_\beta$); 4.66 (m, 1H, (CH)$_\alpha$) 5,32 et 5.7 (m, 1H, (CH)$_{\alpha'}$); 6.9–7.8 (m, 10H, 2 indoles); 8 (m, 1H, CHO (formyl)); 8.2–9 (m, 4H, 3 NH 1H, (CH)$_\alpha$); 6.9–7.8 (m, 10H, 2 indoles); 8 (m, 1H, CHO (formyl)); 8.2–9 (m, 4H, 3 NH (amides) et NH (amine)); 10.87 (m, 2H, 2 N$^1$H (indoles)).

Mass Spectrometry (Electrospray), m/z 489.29 [M+H]$^+$.

Example 4

H-Aib-D-Trp-D-gTrp-C(O)CH$_3$

Boc-D-(N$^i$Boc)Trp-D-g(N$^i$Boc)Trp-H (0.72 mmol; 1 eq.) was dissolved in DMF (20 ml). Then, N,N- diisopropylethylamine (259 ml; 2.1 eq.) and acetic anhydride (749 ml; 1.1 eq.) were added. After 1 hr, the mixture was diluted with ethyl acetate (100 ml) and washed with saturated aqueous sodium hydrogen carbonate (100 ml), aqueous potassium hydrogen sulfate (100 ml, 1M), and saturated aqueous sodium chloride (50 ml). The organic layer was dried over sodium sulfate, filtered and the solvent removed in vacuo. The residue was purified by flash chromatography on silica gel eluting with ethyl acetate/hexane to afford 370 mg (73%) of Boc-D-($N^i$Boc)Trp-D-g($N^i$Boc)Trp-C(O)$CH_3$ as a white solid.

Boc-D-($N^i$Boc)Trp-D-g($N^i$Boc)Trp-C(O)$CH_3$ (350 mg; 0.5 mmol; 1 eq.) was dissolved in a mixture of trifluoroacetic acid (8 ml), anisole (1 ml) and thioanisole (1 ml) for 30 minutes at 0° C. The solvents were removed in vacuo, the residue was stirred with ether and the precipitated TFA, H-D-Trp-D-gTrp-C(O)$CH_3$ was filtered.

In 10 ml of DMF, TFA, H-D-Trp-D-gTrp-C(O)$CH_3$ (0.5 mmol; 1 eq.), Boc-Aib-OH (121 mg; 0.59 mmol; 1.2 eq.), NMM (230 μl; 4.2 eq.) and BOP (265 mg; 1.2 eq.) were successively added. After 1 hr, the mixture was diluted with ethyl acetate (25 ml) and washed with saturated aqueous sodium hydrogen carbonate (50 ml), aqueous potassium hydrogen sulfate (50 ml, 1M), and saturated aqueous sodium chloride (50 ml). The organic layer was dried over sodium sulfate, filtered and the solvent removed in vacuo. The residue was purified by flash chromatography on silica gel eluting with ethyl acetate to afford 249 mg (85%) of Boc-Aib-D-Trp-D-gTrp-C(O)$CH_3$ as a white foam.

Boc-Aib-D-Trp-D-gTrp-C(O)$CH_3$ (249 mg; 0.42 mmol) was dissolved in a mixture of trifluoroacetic acid (8 ml), anisole (1 ml) and thioanisole (1 ml) for 30 minutes at 0° C. The solvents were removed in vacuo, the residue was stirred with ether and the precipitated TFA, H-Aib-D-Trp-D-gTrp-C(O)$CH_3$ was filtered.

The product TFA, H-Aib-D-Trp-D-gTrp-C(O)$CH_3$ (80 mg; 23%) was purified by preparative HPLC (Waters, delta pak, C18, 40×100 mm, 5 mm, 100 A).

$C_{27}H_{32}N_6O_3$, 488 g.mol$^{-1}$.

$^1$H NMR (200 MHZ, DMSO-d$^6$) δ 1.22 (s, 3H, $CH_3$ (Aib)); 1.44 (s, 3H, $CH_3$ (Aib)); 1.8 (s, 3H, C(O)$CH_3$); 3.06 (m, 4H, 2 ($CH_2$)$_β$); 4.6 (m, 1H, (CH)α); 5.6 (m. 1H, (CH)$_{α'}$); 6.9–7.8 (m, 10H, 2 indoles); 7.99 (s, 2H, $NH_2$ (Aib)); 8.2–8.6 (m, 3H, 3 NH (amides)); 10.83 (s, 2H, 2 $N^1$H (indoles)).

Mass Spectrometry (Electrospray), m/z 489.32 [M+H]$^+$.

Example 5

N-Me-Aib-D-Trp-D-gTrp-C(O)$CH_3$

Boc-N-Me-Aib-OH (1.09 g; 5.04 mmol; 4 eq.) was dissolved in methylene chloride (10 ml) and cooled to 0° C. Then, dicyclohexylcarbodiimide (520 mg; 2.52 mmol; 2 eq.) was added. The mixture, after filtration of DCU, was added to a solution containing TFA, H-D-Trp-D-gTrp-C(O)$CH_3$ (940 mg; 1.26 mmol; 1 eq.) and triethylamine (580 ml; 3.3 eq.) in methylene chloride (5 ml). The reaction mixture was slowly warmed to room temperature and stopped after 24 h. The mixture was diluted with ethyl acetate (50 ml) and washed with saturated aqueous sodium hydrogen carbonate (100 ml), aqueous potassium hydrogen sulfate (100 ml, 1M), and saturated aqueous sodium chloride (100 ml). The organic layer was dried over sodium sulfate, filtered and the solvent removed in vacuo. The residue was purified by flash chromatography on silica gel eluting with ethyl acetate/ methanol {9/1} to afford 530 mg (70%) of Boc-N-Me-Aib-D-Trp-D-gTrp-C(O)$CH_3$ as a white foam.

Boc-N-Me-Aib-D-Trp-D-gTrp-C(O)$CH_3$ (530 mg; 0.88 mmol) was dissolved in a mixture of trifluoroacetic acid (8 ml), anisole (1 ml) and thioanisole (1 ml) for 30 minutes at 0° C. The solvents were removed in vacuo, the residue was stirred with ether and the precipitated TFA, N-Me-Aib-D-Trp-D-gTrp-C(O)$CH_3$ was filtered.

The product TFA, N-Me-Aib-D-Trp-D-gTrp-C(O)$CH_3$ (220 mg; 30%) was purified by preparative HPLC (Waters, delta pak, C18, 40×100 mm, 5 mm, 100 A).

$C_{26}H_{34}N_6O_3$, 502 g.mol$^{-1}$.

$^1$H NMR (200 MHZ, DMSO-d$^6$): δ 1.17 (s, 3H, $CH_3$ (Aib)); 1.4 (s, 3H, $CH_3$ (Aib)); 1.78 (s, 3H, C(O)$CH_3$); 2.23 (s, 3H, $NCH_3$); 3.15 (m, 4H, 2 ($CH_2$)$_β$); 4.7 (m, 1H, (CH)$_α$); 5.55 (m, 1H, (CH)$_{α'}$); 6.9–7.9 (m, 10H, 2 indoles); 8.2–8.8 (s, 4H, NH (amine et 3 NH (amides)); 10.8 (s, 2H, 2 $N^1$H (indoles)).

Mass Spectrometry (Electrospray), m/z 503.19 [M+H]$^+$.

Example 6

Pip-D-Trp-D-gTrp-CHO

In 5 ml of DMF, TFA, H-D-Trp-D-gTrp-CHO (230 mg; 0.3 1 mmol; 1 eq.), Boc-($N^4$Boc)Pip-OH (130 mg; 0.38 mmol; 1.2 eq.), NMM (145 μl; 4.2 eq.) and BOP (167 mg; 0.38 mmol; 1.2 eq.) were successively added. After 15 minutes, the reaction was over. The mixture was diluted with ethyl acetate (25 ml) and washed with saturated aqueous sodium hydrogen carbonate (50 ml), aqueous potassium hydrogen sulfate (50 ml, 1M), and saturated aqueous sodium chloride (50 ml). The organic layer was dried over sodium sulfate, filtered and the solvent removed in vacuo to afford Boc-($N^4$Boc)Pip-D-Trp-D-gTrp-CHO as a foam.

Boc-($N^4$Boc)Pip-D-Trp-D-gTrp-CHO (0.31 mmol) was dissolved in a mixture of trifluoroacetic acid (8 ml), anisole (1 ml) and thioanisole (1 ml) for 30 minutes at 0° C. The solvents were removed in vacuo, the residue was stirred with ether and TFA, H-Pip-D-Trp-D-gTrp-CHO was filtered.

The product TFA, H-Pip-D-Trp-D-gTrp-CHO (127 mg; 42%) was purified by preparative HPLC (Waters, delta pak, C18, 40×100 mm, 5 μm, 100 A).

$C_{28}H_{33}N_7O_3$, 515 g.mol$^{-1}$.

$^1$H RMN (200 MHZ, DMSO-d$^6$): δ 1.81 (m, 2H, $CH_2$ (Pip)); 2.3 (m, 2H, $CH_2$ (Pip)); 3.1 (m, 8H, 2 ($CH_2$)$_β$ et 2 $CH_2$ (Pip)); 4.68 (m, 1H, (CH)$_α$); 5.3 et 5.73 (2m, 1H, (CH)$_{α'}$); 6.9–7.7 (m, 10H, 2 indoles); 7.98 (2s, 1H, CHO (formyl)); 8.2–9.2 (m, 6H, $NH_2$ et NH (Pip) et 3 NH (amides)); 10.9 (m, 2H, 2 $N^1$H (indoles)).

Mass Spectrometry (Electrospray), m/z 516.37 [M+H]$^+$, 538.27 [M+Na]$^+$.

Example 7

Pip-D-Trp-D-gTrp-C(O)$CH_3$

In 5 ml of DMF, TFA, H-D-Trp-D-gTrp-C(O)$CH_3$ (218 mg, 0.29 mmol; 1 eq.), Boc-($N^4$Boc)Pip-OH (121 mg; 0.35 mmol; 1.2 eq.), NMM (135 μl; 4.2 eq.) and BOP (155 mg; 0.35 mmol; 1.2 eq.) were successively added. After 15 minutes, the reaction was over. The mixture was diluted with ethyl acetate (25 ml) and washed with saturated aqueous sodium hydrogen carbonate (50 ml), aqueous potassium hydrogen sulfate (50 ml, 1M), and saturated aqueous sodium chloride (50 ml). The organic layer was dried over sodium sulfate, filtered and the solvent removed in vacuo to afford Boc-($N^4$Boc)Pip-D-Trp-D-gTrp-C(O)CH$^3$ as a foam.

Boc-($N^4$Boc)Pip-D-Trp-D-gTrp-C(O)$CH_3$ (0.29 mmol) was dissolved in a mixture of trifluoroacetic acid (8 ml), anisole (1 ml) and thioanisole (1 ml) for 30 minutes at 0° C. The solvents were removed in vacuo, the residue was stirred with ether and the precipitated TFA, H-Pip-D-Trp-D-gTrp-C(O)CH₃ was filtered.

The product TFA, H-Pip-D-Trp-D-gTrp-C(O)CH₃ (135 mg; 47%) was purified by preparative HPLC (Waters, delta pak, C 18, 40×100 mm, 5 μm, 100 A).

$C_{29}H_{35}N_7O_3$, 529 g.mol⁻¹.

¹H RMN (200 MHZ, DMSO-d⁶): δ 1.79 (m, 2H, CH₂ (Pip)); 1.81 (s, 3H, C(O)CH₃); 2.3 (m, 2H, CH₂ (Pip)); 3.1 (m, 8H, 2 (CHi)$_\beta$ et 2 CH₂ (Pip)); 4.7 (m, 1H, (CH)α); 5.6 (m, 1H, (CH)$_\alpha$); 6.9–7.8 (m, 10H, 2 indoles); 8.2–9 (m, 6H, NH₂ et NH (Pip) et 3 NH (amides)); 10.85 (m, 2H, 2 N¹H (indoles)).

Mass Spectrometry (Electrospray), mn/z 530.39 [M+H]⁺, 552.41 [M+Na]⁺.

Example 8

Isonipecotyl-D-Trp-D-gTrp-CHO

In 5 ml of DMF, TFA, H-D-Trp-D-gTrp-CHO (250 mg, 4.1 mmol; 1 eq.), Fmoc-Isonipecotic-OH (144 mg; 4.1 mmol; 1.2 eq.), NMM (158 μl; 4.2 eq.) and BOP (181 mg; 4.1 mmol; 1.2 eq.) were successively added. After 15 minutes, the reaction was over. The mixture was diluted with ethyl acetate (25 ml) and washed with saturated aqueous sodium hydrogen carbonate (50 ml), aqueous potassium hydrogen sulfate (50 ml, 1M), and saturated aqueous sodium chloride (50 ml). The organic layer was dried over sodium sulfate, filtered and the solvent removed in vacuo to afford Fmoc-Isonipecotyl-D-Trp-D-gTrp-CHO as a foam.

Fmoc-Isonipecotyl-D-Trp-D-gTrp-CHO (4.1 mmol) was dissolved in a mixture of DMF (8 ml) and piperidine (2 ml) and allowed to stand for 30 minutes. The solvents were removed in vacuo, the residue was stirred with ether and the precipitated Isonipecotyl-D-Trp-D-gTrp-CHO was filtered.

The product Isonipecotyl-D-Trp-D-gTrp-CHO (81 mg; 28%) was purified by preparative HPLC (Waters, delta pak, C18, 40×100 mm, 5 μm, 100 A).

$C_{28}H_{32}N_6O_3$, 500 g.mol⁻¹.

¹H RMN (200 MHZ, DMSO-d⁶): δ 1.65 (m, 4H, 2 CH₂ (Pip)); 2.4 (m, 1H, CH (Pip)); 2.7–3.3 (m, 8H, 2 (CH₂)$_\beta$ et 2 CH₂ (Pip)); 4.6 (m, 1H, (CH)$_\alpha$); 5.3 et 5.7 (2m, 1H, (CH)$_\alpha$); 6.9–7.7 (m, 10H, 2 indoles); 7.97 (2s, 1H, CHO (formyl)); 8–8.8 (m, 4H, NH (Pip) et 3 NH (amides)); 10.9 (m, 2H, 2 N¹H (indoles)).

Mass Spectrometry (Electrospray), m/z 501.36 [M+H]⁺.

Example 9

Isonipecotyl-D-Trp-D-gTrp-C(O)CH₃

In 5 ml of DMF, TFA, H-D-Tip-D-gTrp-C(O)CH₃ (250 mg, 0.33 mmol; 1 eq.), Fmoc-Isonipecotic-OH (141 mg; 0.4 mmol; 1.2 eq.), NMM (155 μl; 4.2 eq.) and BOP (178 mg; 0.4 mmol; 1.2 eq.) were successively added. After 15 minutes, the reaction was over. The mixture was diluted with ethyl acetate (25 ml) and washed with saturated aqueous sodium hydrogen carbonate (50 ml), aqueous potassium hydrogen sulfate (50 ml, 1M), and saturated aqueous sodium chloride (50 ml). The organic layer was dried over sodium sulfate, filtered and the solvent removed in vacuo to afford Fmoc-Isonipecotyl-D-Trp-D-gTrp-C(O)CH₃ as a foam.

Fmoc-Isonipecotyl-D-Trp-D-gTrp-C(O)CH₃ (0.33 mmol) was dissolved in a mixture of DMF (8 ml) and piperidine (2 ml) and allowed to stand for 30 minutes. The solvents were removed in vacuo, the residue was stirred with ether and the precipitated Isonipecotyl-D-Trp-D-gTrp-C(O)CH₃ was filtered.

The product Isonipecotyl-D-Trp-D-gTrp-C(O)CH3 (65 mg; 13%) was purified by preparative HPLC (Waters, delta pak, C18, 40×100 mm, 5 μm, 100 A).

$C_{29}H_{34}N_6O_3$, 514 g.mol⁻¹.

¹H RMN (200 MHZ, DMSO-d⁶): δ 1.66 (m, 4H, 2 CH₂ (Pip)); 1.79 (s, 3H, C(O)CH₃); 2.7–3.3 (m, 8H, 2 (CH₂)$_\beta$ et 2 CH₂ (Pip)); 4.54 (m, 1H, (CH)$_\alpha$); 6.9–7.7 (m, 10H, 2 indoles); 8–8.6 (m, 4H, NH (Pip) et 3 NH (amides)); 10.82 (m, 2H, 2 N¹H (indoles)).

Mass Spectrometry (Electrospray), m/z 515.44 [M+H]⁺.

Examples 10–62

The following compounds were prepared in similar manners:

Example 10
H-Aib-D-Mrp-gMrp-CHO
Example 11
H-Aib-Trp-gTrp-CHO
Example 12
H-Aib-Trp-D-gTrp-CHO
Example 13
H-Aib-(D)-Trp-gTrp-CHO
Example 14
N-Me-D-Trp-gTrp-CHO
Example 15
N-Methylsulfonyl-D-Trp-gTrp-CHO
Example 16
N-Phenylsulfonyl-D-Trp-gTip-CHO
Example 17
N-(3-Methyl-butanoyl)-D-Trp-gTrp-CO—CH₃
Example 18
N-(3-Methyl-butanoyl)-D-Trp-gTrp-CHO
Example 19
Aib-D-Trp-gTrp-CO—CH₂—CH₃
Example 20
Aib-D-Trp-gTrp-CO—CH₂—CH(CH₃)—CH₃
Example 21
Aib-D-Trp-gTrp-CO—CH₂-phenyl
Example 22
Aib-D-Trp-gTrp-CO-piperidin-4-yl
Example 23
Aib-D-Trp-gTrp-CO—CH₂-pyrrol-3-yl
Example 24
Aib-D-Trp-gTrp-CO—CH₂—CH₂-cyclohexyl
Example 25
N-Me-Aib-D-Trp-gTrp-CO—CH₂—CH₃
Example 26
N-Me-Aib-D-Trp-gTrp-CO—CH₂—CH(CH₃)—CH₃
Example 27
N-Me-Aib-D-Trp-gTrp-CO—CH₂-phenyl
Example 28
N-Me-Aib-D-Trp-gTrp-CO—CH₂-pyrrol-3-yl
Example 29
N-Me-Aib-D-Trp-gTrp-CO—CH₂—CH₂-cyclohexyl
Example 30
Aib-D-Trp-gTrp-CHO
Example 31
N-(3-amino-3-methyl-butanoyl)-D-Trp-gTrp-CO—CH₃

Example 32

N-Acetyl-D-Trp-gTrp-CHO

Example 33

N-Acetyl-D-Trp-gTrp-CO—CH$_3$

Example 34

N-Formyl-D-Trp-gTrp-CHO

Example 35

N-Formyl-D-Trp-gTrp-CO—CH$_3$

Example 36

N-(1,1-dimethyl-2-amino-2-keto-ethyl)-D-Trp-gTrp-CHO

Example 37

N-(2-amino-2-methyl-propyl)-D-Trp-gTrp-CHO

Example 38

N-(2-amino-2-methyl-propyl)-D-Trp-gTrp-CO—CH$_3$

Example 39

N-Me-Aib-D-Trp-D-gTrp-Isonipecotyl

Example 40

N-Me-Aib-D-Trp-N-Me-D-gTrp-C(O)CH$_3$

Example 41

H-Aib-D-Trp-N-Me-D-gTip-C(O)CH$_3$

Example 42

H-Aib-(D)-1-Nal-g-(D)-1-Nal-formyl $C_{30}H_{32}N_4O_3$, 496 g.mol$^{-1}$.

$^1$H RMN (200 MHz, DMSO-d$^6$): δ 1.14 and 1.4 (2m, 6H, 2 CH$_3$(Aib)); 3.17–3.55 (m, 4H, 2 (CH$_2$)$_β$); 4.82 (m, 1H, CHα); 5.5 and 5.82 (2m, 1H, CHα); 7.36–7.64 (m, 7H); 8.25–9.45 (m, 5H).

Mass Spectrometry (FAB), m/z 497 [M+H]$^+$.

Analytic HPLC (Delta Pak 5 μ C18 100A, 1 ml/min, 214 nm, eluent: H$_2$O/ACN 0.1% TFA, gradient 0 to 100% ACN in 50 min), tr=20.28 min, 99%. Freezedried Compound.

Example 43

H-Aib-(D)-2-Nal-g-(D)-2-Nal-formyl $C_{30}H_{32}N_4O_3$, 496 g.mol$^{-1}$.

$^1$H RMN (200 MHz, DMSO-d$^6$): δ 1.18 and 1.36 (2m, 6H, 2 CH$_3$(Aib)); 2.84–3.3 (m,4H, 2 (CH$_2$)$_β$); 4.7 (m, 1H, CHα); 5.45 and 5.73 (2m, 1H, CHα); 7.47–7.51 (m, 11H); 8.36–9.11 (m, 3H).

Mass Spectrometry (FAB), m/z 497 [M+H]$^+$.

Analytic HPLC (Delta Pak 5 μ C18 100A, 1 ml/min, 214 nm, eluent: H$_2$O/ACN 0.1% TFA, gradient 0 to 100% ACN in 50 min), tr=20.26 mm, 95%. Freezedried Compound.

Example 44

H-Aib-(D)-1-Nal-(D)-gTrp-formyl $C_{28}H_3,N_5O_3$, 485 g.mol$^{-1}$.

$^1$H RMN (200 MHz, DMSO-d$^6$): δ 1.15 and 1.42 (2m, 6H, 2 CH$_3$(Aib)); 3.11–3.3 and 3.54–3.7 (m, 4H, 2 (CH$_2$)$_β$); 4.81 (m, 1H, CH$_α$); 5.4 and 5.74 (2m, 1H, CH$_α$); 7.06–7.2 (m, 3H); 7.34–7.65 (m, 6H); 7.91–8.1 (m, 4H); 8.2–8.4 (m, 1H); 8.55–9.5 (m, 1H, N$^1$H).

Mass Spectrometry (FAB), m/z 486 [M+H]$^+$.

Analytic HPLC (Delta Pak 5 μ C18 100A, 1 ml/min, 214 nm, eluent: H$_2$O/ACN 0.1% TFA, gradient 0 to 100% ACN in 50 min), tr=17.33 mm, 92%. Freezedried Compound.

Example 45

H-Aib-(D)-2-Nal-(D)-gTrp-formyl $C_{28}H_{31}N_5O_3$, 485 g.mol$^{-1}$.

$^1$H RMN (200 MHz, DMSO-d$^6$): δ 1.19 and 1.45 (2m, 6H, 2 CH$_3$(Aib)); 2.93–3.3 (m, 4H, 2 (CH$_2$)$_β$); 4.71 (m, 1H, CH$_α$); 5.35 and 5.7 (2m, 1H, CH$_α$); 7.05–7.1 (m, 2H); 7.2–7.34 (m, 1H); 7.47–7.53 (m, 4H); 7.64 (m, 1H); 7.78–8 (m, 8H); 8.48–9.37 (m, 2H); 10.88–11.04 (m, 1H,N$^1$H).

Mass Spectrometry (FAB), m/z 486 [M+H]$^+$.

Analytic HPLC (Delta Pak 5 μ C18 100A, 1 ml/min, 214 nm, eluent: H$_2$O/ACN 0.1% TFA, gradient 0 to 100% ACN in 50 min), tr=17.30 min, 95%. Freezedried Compound.

Example 46

H-Aib-(D)-Trp-g-(D)-1-Nal-formyl $C_{28}H_{31}N_5O_3$, 485 g.mol$^{-1}$.

$^1$H RMN (200 MHz, DMSO-d$^6$): δ 1.23 and 1.41 (2m, 6H, 2 CH$_3$(Aib)); 2.92–3.15 (m 2H, (CH$_2$)$_β$); 3.4–3.6 (m, 2H, (CH$_2$)$_β$); 4.63 (m, 1H, CH$_α$); 5.44 and 5.79 (2m, 1H, CH$_{α'}$); 6.99–7.15 (m, 3H); 7.33 (m, 1H); 7.45–8.1 (m, 11H); 8.34–9.37 (m, 3H); 10.83 (m 1H).

Mass Spectrometry (FAB), m/z 486 [M+H]$^+$.

Analytic HPLC (Symmetry shield 3.5 μ C18 100A, 1 ml/min, 214 nm, eluent: H$_2$O/ACN 0.1% TFA, gradient 0 to 60% ACN in 15 min then 60 to 100% ACN in 3 min), tr=10.00 min, 99%. Freezedried Compound.

Example 47

H-Aib-D-Trp-g-D-2-Nal-formyl $C_{28}H_{31}N_5O_3$, 485 g.mol$^{-1}$.

$^1$H RMN (200 MHz, DMSO-d$^6$): δ 1.22 and 1.43 (2m, 6H, 2 CH$_3$ (Aib)); 2.85–3.3 (m, 4H, 2 CH$_2$); 4.64 (m, 1H, CH$_α$); 5.37 and 5.72 (2m, 1H, CH$_{α'}$); 6.97–7.13 (m, 3H); 7.32 (m,1H); 7.44–7.54 (m, 3H); 7.66 (d, 1H); 7.78 (m, 1H); 7.86–8.02 (m, 7H); 8.33–9.4 (m, 2H); 10.82 (m, 1H, N$^1$H).

Mass Spectrometry (FAB), m/z 486 [M+H]$^+$.

Analytic HPLC (Delta pak 5 μ C18 100A, 1 ml/min, 214 nm, eluent: H$_2$O/ACN 0.1% TFA, gradient 0 to 100% ACN in 25 min), tr=9.00 min, 99%. Freezedried Compound.

Example 48

H-Aib-(D)-Trp-(D)-3(R/S)-Dht-formyl $C_{26}H_{32}N_6O_3$, 476 g.mol$^{-1}$.

$^1$H RMN (400 MHz, DMSO-d$^6$): δ 1.12 (s, 3H, CH$_3$ (Aib)); 1.32 (s, 3H, CH$_3$(Aib)); 1.73 (m, 1H, CH$_2$); 2.01 (m,

1H, CH$_2$); 2.9 (m, 1H); 3.03 (m, 1H); 3.13 (m, 2H); 3.54 (m, 1H); 4.47 (m, 1H, CH$_\alpha$); 5.10 and 5.52 (2m, 1H, CH$_{\alpha'}$); 6.71–8.83 (m, 16H 5H (Trp), 4H (Dht), 3 NH (amides), NH and NH$_2$ (amines), formyl); 10.7 (m, 1H, N$^1$H).

Mass Spectrometry (Electrospray), m/z 477.46 [M+H]$^+$ 499.42 [M+Na]$^+$; 953.51 [2M+H]$^+$.

Analytic HPLC (Delta Pak 5 $\mu$ C18 100A, 1 ml/min, 214 nm, eluent: H$_2$O/ACN 0.1% TFA, gradient 0 to 100% ACN in 50 min), tr=9.40 min, 98%. Freezedried Compound.

Example 49

H-Aib-(D)-3(R/S)-Dht-g-(D)-Trp-formyl

C$_{26}$H$_{32}$N$_6$O$_3$, 476 g.mol$^{-3}$.

RMN $^1$H(400 MHz, DMSO-d$^6$): δ 1.58 (s, 3H, CH$_3$ (Aib)); 1.85 (m, 1H, CH$_2$); 2.2 (m, 1H, CH$_2$); 3.1 (d, 2H); 3.35 (m, 2H); 3.56 (m, 1H); 3.7 (m, 1H); 4.5 (m, 1H, CH$_\alpha$); 5.33 and 5.71 (2m, 1H, CH$_{\alpha'}$); 6.88–8.91 (m, 16H, 5H (Trp), 4H (Dht), 3 NH (amides), NH and NH$_2$ (amines), formyl); 10.92 and 10.97 (2s, 1H, N$^1$H).

Mass Spectrometry (Electrospray), m/z 477.33 [M+I]$^+$; 499.42 [M+Na]$^+$ 953.51 [2M+H]$^+$.

Analytic HPLC (Delta Pak 5 $\mu$ C18 100A, 1 ml/min, 214 nm, eluent: H$_2$O/ACN 0.1% TFA, gradient 0 to 100% ACN in 50 min), tr=10.35 mm, 98%. Freezedried Compound.

Example 50

N(Me)-Aib-(D)-Trp-(D)-3(R/S)-gDht-acetyl

C$_{28}$H$_{36}$N$_6$O$_3$, 504 g.mol$^{-1}$.

$^1$H RMN (400 MHz, DMSO-d$^6$): δ 1.42 (s, 3H, CH$_3$ (Aib)); 1.63 (s, 3H, CH$_3$ (Aib))2.72 (m, 3H, acetyl); 2.4 (m, 2H, CH$_2$); 2.5 (m, 3H, NCH$_3$); 3.2–3.5 (m, 4H); 3.85 (m, 1H); 4.85 (m, 1H, CH$_\alpha$); 5.76 (m, 1H, CH$_{\alpha'}$); 7.04–8.86 (m, 14H, 5H (Trp), 4H (Dht), 3 NH (amides), 2 NH (amines)); 11.02 (2s, 1H, N$^1$H).

Mass Spectrometry (Electrospray), m/z 505,31 [M+H]$^+$; 527,70 [M+Na]$^+$.

Analytic HPLC (Delta Pak 5 $\mu$ C18 100A, 1 ml/min, 214 nm, eluent: H$_2$O/ACN 0.1% TFA, gradient 0 to 100% ACN in 50 min), tr=10.20 min, 98%. Freezedried Compound.

Example 51

N(Me)-Aib-(D)-3(R/S)-Dht-(D)-gTrp-acetyl

C$_{28}$H$_{36}$N$_6$O$_3$, 504 g.mol$^{-1}$.

$^1$H RMN (400 MHz, DMSO-d$^6$): δ 1.58 (s, 6H, 2 CH$_3$ (Aib)); 1.81 (m, 3H, acetyl); 1.98 (m, 1H, CH$_2$); 2.24 (m, 1H, CH$_2$); 2.54 (m, 3H, NCH$_3$); 3.08 (d, 2H); 3.31 (m, 2H); 3.4 (m, 1H); 3.59 (m, 1H); 3.71 (m, 1H); 4.52 (m, 1H, CH$_\alpha$); 5.61 (m, 1H, CH$_\alpha$); 5.61 (m, 1H, CH$_{\alpha'}$); 6.9–8.92 (m, 14H, 5H (Trp), 4H (Dht), 3 NH (amides), 2 NH (amines)); 10.88 (s, 1H, N$^1$H).

Mass Spectrometry (Electrospray), m/z 505.43 [M+H]$^+$; 527.52 [M+Na]$^+$.

Analytic HPLC (Delta Pak 5 $\mu$ C18 100A, 1 ml/min, 214 nm, eluent: H$_2$O/ACN 0.1% TFA, gradient 0 to 100% ACN in 50 min), tr=11 min, 98%. Freezedried Compound.

Example 52

N(Me)$_2$-Aib-(D)-Trp-(D)-gTrp-formyl

C$_{28}$H$_{36}$N$_6$O$_3$, 502 g.mol$^{-1}$.

$^1$H RMN (400 MHz, DMSO-d$^6$): δ 1.2 (s, 3H, CH$_3$ (Aib)); 1.39 (s, 3H, CH$_3$ (Aib)); 2.29 (m, 3H, NCH$_3$); 2.99–3.33 (m, 4H, 2 (CH$_2$)$_\beta$); 4.68 (m, 1H, CH)$_\alpha$); 5.3 and 5.69 (m, 1H, CH)$_{\alpha'}$); 6.97–7.72 (m, 10H, 2 indoles); 7.97 (2s, 1H, formyl); 8.2–9.47 (m, 3H, 3 NH (amides)); 10.85 (m, 2H, 2 NH (indoles)).

Mass Spectrometry (Electrospray), m/z 503.45 [M+H]$^+$.

Analytic HPLC (Symmetry shield 3.5 $\mu$ C18 100A, 1 ml/min, 214 nm, eluent: H$_2$O/ACN 0.1% TFA, gradient 0 to 100% ACN in 15 min), tr=6.63 min, 99%. Freezedried Compound.

Example 53

N(Me)$_2$-Aib-(D)-Trp-(D)-gTrp-acetyl

C$_{29}$H$_{36}$N$_6$O$_3$, 516 g.mol$^{-1}$.

$^1$H RMN (200 MHz, DMSO-d$^6$) δ 1.22 (s, 3H, CH$_3$ (Aib)); 1.4 (s, 3H, CH$_3$ (Aib)); 1.8 (s, 3H, acetyl); 2.28 (d, 3H, NCH$_3$); 2.96–3.22 (m, 4H, 2 (CH$_2$)$_\beta$); 4.7 (m, 1H, (CH)$_\alpha$); 5.60 (m, 1H, (CH)$_{\alpha'}$); 6.98–7.75 (m, 10H, 2 indoles); 8.2–9.47 (m, 3H, 3 NH (amides)), 10.84 (m, 2H, 2 NH (indoles)).

Mass Spectrometry (Electrospray), m/z 517.34 [M+H]$^+$.

Analytic HPLC (Symmetry shield 3.5 $\mu$ C18 100A, 1 ml/min, 214 nm, eluent: H$_2$O/ACN 0.1% TFA, gradient 0 to 100% ACN in 15 min), tr=7.07 mm, 99%. Freezedried Compound.

Example 54

H-Acc$^3$-(D)-Trp-(D)-gTrp-formyl

C$_{26}$H$_{28}$N$_6$O$_3$, 472 g.mol$^{-1}$.

$^1$H RMN (400 MHz, DMSO-d$^6$): δ 1.11 and 1.5 (2m, 4H, 2 CH$_2$ (Acc$^3$)); 2.9–3.12 (m, 4H, 2 (CH$_2$)$_\beta$); 4.6 (m, 1H, CH$_\alpha$); 5.3 and 5.7 (2m, 1H, CH$_{\alpha'}$); 6.97–7.17 (m, 6H, indoles); 7.32 (m, 2H, indoles); 7.62–7.72 (m, 2H, indoles); 7.97 (2s, 1H, formyl); 8.27–8.92 (m, 5H, 3 NH (amides) and NH$_2$ (amine)); 10.80–10.90 (4s, 2H, 2 N$^1$H).

Mass Spectrometry (Electrospray), m/z 473.22 [M+H]$^+$; 495.15 [M+Na]$^+$ 945.47 [2M+H]$^+$; 967.32 [2M+Na]$^+$.

Analytic HPLC (Delta Pak 5 $\mu$ C18 100A, 1 ml/min, 214 nm, eluent: H$_2$O/ACN 0.1% TFA, gradient 0 to 100% ACN in 50 min), tr=14.20 min, 98%. Freezedried Compound.

Example 55

H-Acc$^5$-(D)-Trp-(D)-gTrp-formyl

C$_{26}$H$_{28}$N$_6$O$_3$, 472 g.mol$^{-1}$.

$^1$H RMN (400 MHz, DMSO-d$^6$): δ 1.51 and 2.31 (m, 8H, 4 CH$_2$ (Acc$^5$)); 2.97–3.18 (m, 4H, 2 (CH$_2$)$_\beta$); 4.64 (m, 1H, CH$_\alpha$); 5.31 and 5.69 (2m, 1H, CH$_{\alpha'}$); 6.96–7.34 (m, 8 H, indoles); 7.62–7.74 (m, 2H, indoles); 7.96 (m, 3H, formyl and NH$_2$ (amine)); 8.48–8.96 (m, 3H, 3 NH (amides); 10.80–10.90 (4s, 2H, 2 N$^1$H).

Mass Spectrometry (Electrospray), m/z 501.31 [M+H]$^+$; 523.42 [M+Na]$^+$; 101.37 [2M+H]$^+$.

Analytic HPLC (Delta Pak 5 $\mu$ C18 100A, 1 ml/min, 214 nm, eluent: H$_2$O/ACN 0.1% TFA, gradient 0 to 100% ACN in 50 min), tr=15.35 min, 98%. Freezedried Compound.

Example 56

H-Acc$^6$-(D)-Trp-(D)-gTrp-formyl

C$_{26}$H$_{28}$N$_6$O$_3$, 472 g.mol$^{-1}$.

$^1$H RMN (400 MHz, DMSO-d$^6$): δ 1.29–1.57 (m, 8H, 4 CH$_2$ (Acc$^6$)); 1.89 and 2.04 (2m, 2H, CH$_2$(Acc$^6$)); 2.95–3.17

(m, 4H, 2 (CH$_2$)$_\beta$); 4.61 (m, 1H, CH$_\alpha$); 5.3 and 5.68 (2m, 1H, CH$_{\alpha'}$); 6.95–7.21 (m, 6H, indoles); 7.32 (m, 2H, indoles); 7.6 (m, 2H, indoles); 7.74 (m, 2H, indoles); 7.96 (m, 3H, formyl and NH$_2$ (amine)); 8.18–8.67 (m, 5H, 3 NH (amides)); 10.77–10.89 (4s,2H, 2N$^1$H).

Mass Spectrometry (Electrospray), m/z 515.11 [M+H]$^+$.

Analytic HPLC (Delta Pak 5 $\mu$ C18 100A, 1 ml/min, 214 nm, eluent: H$_2$O/ACN 0.1% TFA, gradient 0 to 100% ACN in 50 min), tr=15.9 min, 97%. Freezedried Compound.

Example 57

H-Dpg-(D)-Trp-(D)-gTrp-formyl

C$_{26}$H$_{28}$N$_6$O$_3$, 530 g.mol$^{-1}$.

$^1$H RMN (400 MHz, DMSO-d$^6$): δ 0 (m, 1H, Dpg); 0.40 (m, 3H, Dpg); 0.70 (m, 4H, Dpg); 1.01–1.51 (m, 5H, Dpg); 1.76 (m, 1H, Dpg); 2.82–2.95 (m, 4H, 2 (CH$_2$)$_\beta$); 4.59 (m, 1H, CH$_\alpha$); 5.3 and 5.54 (2m, 1H, CH$_{\alpha'}$); 6.81–7.09 (m, 6H, indoles); 7.19 (m, 2H, indoles); 7.48 (m, 1H, indoles); 7.6–7.68 (m, 5H, 1H (indoles), formyl and NH$_2$ (amine); 7.83–8.82 (m,3H, 3 NH (amides)); 10.69 and 10.76 (2m, 2H, 2N$^1$H).

Mass Spectrometry (Electrospray), m/z 531.24 [M+I]$^+$.

Analytic HPLC (Delta Pak 5 $\mu$ C18 100A, 1 ml/min, 214 nm, eluent: H$_2$O/ACN 0.1% TFA, gradment 0 to 100% ACN in 50 mm), tr=15.35 mm, 98%. Freezedried Compound.

Example 58

H-Aib-(D)-Trp-(D)-gTrp-C(O)NHCH$_2$CH$_3$

C$_{26}$H$_{25}$N$_7$O$_3$, 517 g.mol$^{-1}$.

$^1$H RMN (400 MHz, DMSO-d$^6$): δ 0.94 (t, 3H, NHCH$_2$CH$_3$); 1.01 (s, 3H, CH$_3$ (Aib)); 1.08 (s, 3H, CH$_3$ (Aib)); 1.8 (sl, 2H, NH$_2$); 2.95–3.15 (m, 6H, 2 (CH$_2$)$_\beta$ and NHCH$_2$CH$_3$); 4.43 (m, 1H, CH$^\alpha$); 5.39 (m, 1H, CH$_{\alpha'}$); 6.02 (m, 1H); 6.22 (m, 1H); 6.9–7.56 (m, 1H); 6.22 (m, 1H); 6.9–7.56 (m, 10 H, indoles); 8 (m, 1H); 8.31 (m, 1H); 10.77 and 10.79 (2s, 2H, 2N$^1$H).

Mass Spectrometry (Electrospray), m/z 518.4 [M+H]$^+$; 540.3 [M+Na]$^+$.

Analytic HPLC (Symmetry shield 3.5 $\mu$ C18 100A, 1 ml/min, 214 nm, eluent: H$_2$O/ACN 0.1% TFA, gradient 0 to 100% ACN in 15 min), tr=7.12 min, 99%. Freezedried Compound.

Example 59

N-Me-Aib-(D)-Trp-(D)-gTrp-C(O)NHCH$_2$CH$_3$

Example 60

H-Aib-(R)—Me-Trp-(D)-gTrp-formyl

Example 61

H-Aib-(D)-Trp-(R)-Me-gTrp-formyl

Example 62

H-Me-Aib-(D)-Trp-(R)-Me-gTrp-acetyl

Example 63

Evaluation of the Growth Hormone Releasing Activity of New Growth Hormone Secretagogues in the Infant Rat Animals Male 10-day-old Sprague Dawley rats, about 25 g body weight were used.

Pups were received on the fifth day after birth and were housed under controlled conditions (22±2° C., 65% humidity and artificial light from 06.00 to 20.00 h). A standard dry diet and water were available ad libitum to the dams.

Experimental Procedure

One hour before the experiments, pups were separated from their respective dams and were divided randomly into groups of eight each.

Pups were acutely challenged subcutaneously with 100 $\mu$l of solvent (DMSO, final dilution 1:300 in physiological saline), hexarelin (Tyr-Ala-His-D-Mrp-Ala-Trp-D-Phe-Lys-NH$_2$, used as a reference drug), or new compounds (300 $\mu$g/kg) and killed by decapitation 15 min later.

Trunk blood was collected and centrifuged immediately. Plasma samples were stored at −20° C. until assayed for the determination of plasma GH concentrations.

Growth hormone concentrations in plasma were measured by RIA using materials provided by the National Institute of Diabetes, Digestive and Kidney Diseases (NIDDK) of the National Institute of Health U.S.A.

Values were expressed in terms of the NIDDK-rat-GH-RP-2 standard (potency 21 U/mg) as ng/ml of plasma.

The minimum detectable value of rat GH was about 1.0 ng/ml, and intraassay variability was about 6%.

The obtained results of several test series, wherein the in vivo activity in the rat was determined, are listed in tables 1 to 10.

TABLE 1

| Example | Structure | GH ng/ml |
|---|---|---|
| 1 | H-Aib-D-Trp-D-gTrp-CHO | 158.8 ± 39.4 |
| 13 | H-Aib-D-Trp-gTrp-CHO | 58 ± 6.3 |
| SOLVENT | | 15.0 ± 8.0 |
| HEXARELIN | Tyr-Ala-His-D-Mrp-Ala-Trp-D-Phe-Lys-NH$_2$ | 202 ± 32.7 |

TABLE 2

| Example | Structure | GH ng/ml |
|---|---|---|
| 3 | N-Me-Aib-D-Trp-D-gTrp-CHO | 86.6 ± 12.6 |
| 4 | H-Aib-D-Trp-D-gTrp-C(O)CH$_3$ | 104.7 ± 13.5 |
| 5 | N-Me-Aib-D-Trp-D-gTrp-C(O)CH$_3$ | 175.5 ± 37.2 |
| SOLVENT | | 20.7 ± 0.9 |
| HEXARELIN | Tyr-Ala-His-D-Mrp-Ala-Trp-D-Phe-Lys-NH$_2$ | 134.5 ± 27.2 |

TABLE 3

| Example | Structure | GH ng/ml |
|---|---|---|
| 6 | Pip-D-Trp-D-gTrp-CHO | 109.7 ± 10.1 |
| 7 | Pip-D-Trp-D-gTrp-C(O)CH$_3$ | 53.1 ± 6.6 |
| 8 | Isonipecotyl-D-Trp-D-gTrp-CHO | 94.2 ± 8.6 |
| 9 | Isonipecotyl-D-Trp-D-gTrp-C(O)CH$_3$ | 61.2 ± 10.8 |
| 19 | Aib-D-Trp-gTrp-CO-CH$_2$-CH$_3$ | 79.8 ± 22.4 |
| 22 | Aib-D-Trp-gTrp-CO-Piperidin-4-yl | 153.6 ± 30.6 |
| SOLVENT | | 22.3 ± 5 |
| HEXARELIN | Tyr-Ala-His-D-Mrp-Ala-Trp-D-Phe-Lys-NH$_2$ | 114.7 ± 8.4 |

TABLE 4

| Example | Structure | GH ng/ml |
|---|---|---|
| 39 | N-Me-Aib-D-Trp-D-gTrp- Isonipecotyl | 97.1 ± 21.0 |
| 40 | N-Me-Aib-D-Trp-N-Me-D-gTrp-C(O)CH$_3$ | 188.2 ± 28.5 |
| 41 | H-Aib-D-Trp-N-Me-D-gTrp-C(O)CH$_3$ | 75.4 ± 15.0 |
| SOLVENT | | 10.55 ± 2.65 |
| HEXARELIN | Tyr-Ala-His-D-Mrp-Ala-Trp-D-Phe-Lys-NH$_2$ | 114.5 ± 12.9 |

TABLE 5

| Example | Structure | GH ng/ml |
|---|---|---|
| 42 | H-Aib-(D)-1-Nal-g-(D)-1-Nal-formyl | 25.05 ± 06.00 |
| 43 | H-Aib-(D)-2-Nal-g-(D)-2-Nal-formyl | 37.33 ± 19.74 |
| 44 | H-Aib-(D)-1-Nal-(D)-gTrp-formyl | 15.04 ± 03.30 |
| 45 | H-Aib-(D)-2-Nal-(D)-gTrp-formyl | 13.91 ± 03.87 |
| 46 | H-Aib-(D)-Trp-g-(D)-1-Nal-formyl | 8.26 ± 01.09 |
| 47 | H-Aib-(D)-Trp-g-(D)-2-Nal-formyl | 9.04 ± 04.03 |
| SOLVENT | | 6.49 ± 01.18 |
| HEXARELIN | | 276.01 ± 23.5 |

TABLE 6

| Example | Structure | GH ng/ml |
|---|---|---|
| 48 | H-Aib-(D)-Trp-(D)-3(R/S)-gDht-formyl | 17.49 ± 2.40 |
| 49 | H-Aib-(D)-3(R/S)-Dht-(D)-gTrp-formyl | 24.35 ± 4.85 |
| 50 | N(Me)-Aib-(D)-Trp-(D)-3(R/S)-gDht-acetyl | 11.17 ± 1.35 |
| 51 | N(Me)-Aib-(D)-3(R/S)-Dht-(D)-gTrp-acetyl | 19.38 ± 4.16 |
| SOLVENT | | 14.65 ± 0.92 |
| HEXARELIN | | 91.61 ± 4.09 |

TABLE 7

| Example | Structure | GH ng/ml |
|---|---|---|
| 52 | N(Me)$_2$-Aib-(D)-Trp-(D)-gTrp-formyl | 121.43 ± 29 |
| 53 | N(Me)$_2$-Aib-(D)-Trp-(D)-gTrp-acetyl | 26.80 ± 5.64 |
| SOLVENT | | 7.89 ± 1.77 |
| HEXARELIN | | 172.5 ± 38.53 |

TABLE 8

| Example | Structure | GH ng/ml |
|---|---|---|
| 60 | H-Aib-(R)-Me-Trp-(D)-gTrp-formyl | 21.02 ± 3.43 |
| 61 | H-Aib-(D)-Trp-(R)-Me-gTrp-formyl | 152.28 ± 43.76 |
| 62 | H-Me-Aib-(D)-Trp-(R)-Me-gTrp-acetyl | 171.78 ± 10.32 |
| SOLVENT | | 7.89 ± 1.77 |
| HEXARELIN | | 172.5 ± 38.53 |

TABLE 9

| Example | Structure | GH ng/ml |
|---|---|---|
| 54 | H-Acc$^3$-(D)-Trp-(D)-gTrp-formyl | 7.89 ± 3.20 |
| 55 | H-Acc$^5$-(D)-Trp-(D)-gTrp-formyl | 11.46 ± 1.18 |
| 56 | H-Acc$^6$-(D)-Trp-(D)-gTrp-formyl | 8.49 ± 0.40 |
| 57 | H-Dpg-(D)-Trp-(D)-gTrp-formyl | 18.38 ± 2.88 |
| SOLVENT | | 17.32 ± 1.70 |
| HEXARELIN | | 89.91 ± 3.04 |

TABLE 10

| Example | Structure | GH ng/ml |
|---|---|---|
| 58 | H-Aib-(D)-Trp-(D)-gTrp-C(O)NHCH$_2$CH$_3$ | 376.48 ± 43.24 |
| 59 | N-Me-Aib-(D)-Trp-(D)-gTrp-C(O)NHCH$_2$CH$_3$ | 179.53 ± 24.65 |
| SOLVENT | | 7.89 ± 1.77 |
| HEXARELIN | | 172.5 ± 38.53 |

Furthermore the time dependence of the oral activity in the dog (1 mg/kg; per os) was estimated for example 1 (H-Aib-D-Trp-D-gTrp-CHO). Well-trained beagles of either sex, >10 year, 10–15 kg by weight, were used. Animals were fed normal dry food with water ad libitum and were on a 12 h-light/12 h-dark regimen with on at 7.00. The compound was administered orally to the dogs which had fasted since 16.00 of the preceding day. Blood samples were taken 20 min before administration, at administration and 15, 30, 60, 90, 120 and 180 min after administration. The results are given in table 11.

TABLE 11

| Example 1 t (min) | NAME OF THE DOG ||||||| MEAN VALUE | SEM |
| | DAKOTA | JORMA | RAZ DEGAN | FORREST LEE | MARKUS | TAYLOR | | |
| | Concentration GH (ng/ml) |||||| | |
|---|---|---|---|---|---|---|---|---|
| −20 | 0.48 | 3.58 | 2.14 | 1.43 | 2.45 | 2.32 | 2.07 | 0.38 |
| 0 | 0.35 | 2.75 | 1.64 | 2.01 | 2.55 | 1.41 | 1.79 | 1.03 |
| 15 | 2.11 | 8.91 | 3.58 | 6.38 | 6.11 | 4.8 | 5.32 | 1.02 |
| 30 | 0.54 | 6.85 | 6.37 | 8.48 | 6.9 | 3.89 | 5.5 | 1.07 |
| 60 | 0.17 | 2.65 | 3.02 | 4.41 | 6.51 | 4.34 | 3.52 | 0.84 |
| 90 | 0.4 | 2.47 | 2.61 | 6.42 | 5.18 | 4.43 | 3.59 | 0.66 |
| 120 | 3.58 | 2.48 | 1.94 | 3.71 | 4.54 | 4.28 | 3.42 | 0.38 |
| 180 | 3.46 | 2.82 | 1.49 | 3.18 | 4.12 | 3.18 | 3.04 | 0.36 |
| AUC | 328.53 | 658.38 | 510.64 | 888.91 | 944.26 | 721.34 | 675.35 | 94.47 |

SEM = Standard deviation
AUC = Area under the curve

What is claimed is:

1. A compound which is

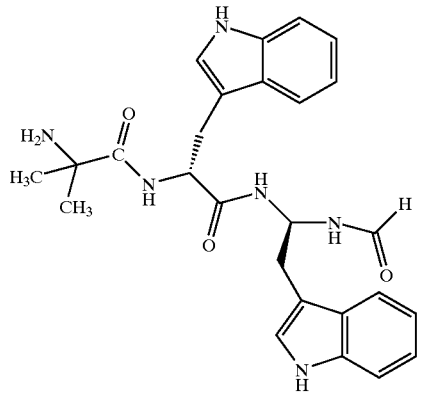

2. A pharmaceutical composition, comprising a compound of claim 1.

3. The composition of claim 2, in combination with a pharmaceutically acceptable carrier.

4. The composition of claim 2, in combination with an additional growth hormone secretagogue.

5. A method for elevating the plasma level of growth hormone in a mammal comprising administering to a mammal a therapeutically effective amount of a compound according to claim 1 so as to elevate the plasma level of growth hormone.

6. A method for the treatment of growth hormone secretion deficiency comprising administering to a mammal a therapeutically effective amount of a compound according to claim 1 so as to treat the growth hormone secretion deficiency.

7. A method for the treatment of growth retardation in a child comprising administering to a patient a therapeutically effective amount of a compound according to claim 1 so as to treat the growth retardation.

8. A method for the treatment of metabolic disorders associated with growth hormone secretion deficiency comprising administering to a patient a therapeutically effective amount of a compound according to claim 1 so as to treat the metabolic disorder.

9. The compound of claim 1 in the form a salt thereof.

* * * * *

UNITED STATES PATENT AND TRADEMARK OFFICE
CERTIFICATE OF CORRECTION

PATENT NO. : 6,861,409 B2
DATED : March 1, 2005
INVENTOR(S) : Martinez et al.

It is certified that error appears in the above-identified patent and that said Letters Patent is hereby corrected as shown below:

Column 23,
Line 24, after "A compound", delete "which is" and insert --having the following structure --.
Line 43, after "A pharmaceutical composition, comprising", delete "a" and insert -- the --.

Column 24,
Line 27, after "a therapeutically effective amount of" , delete "a" and insert -- the --.
Line 32, after "therapeutically effective amount of", delete "a" and insert -- the --.
Line 37, after "effective amount of", delete "a" and insert -- the --.
Line 42, after "amount of", delete "a" and insert -- the --.

Signed and Sealed this

Thirty-first Day of May, 2005

JON W. DUDAS
*Director of the United States Patent and Trademark Office*